(12) United States Patent
Pathi et al.

(10) Patent No.: US 8,030,491 B2
(45) Date of Patent: Oct. 4, 2011

(54) PROCESS AND INTERMEDIATE FOR PREPARATION OF DONEPEZIL

(75) Inventors: Srinivas Laxminarayan Pathi, Karnataka (IN); Vinod Acharya, Gujarat (IN); Dharmaraj Ramachandra Rao, Maharashtra (IN); Rajendra Narayanrao Kankan, Maharashtra (IN)

(73) Assignee: Cipla Limited, Mumbai (IN)

( * ) Notice: Subject to any disclaimer, the term of this patent is extended or adjusted under 35 U.S.C. 154(b) by 612 days.

(21) Appl. No.: 12/159,770

(22) PCT Filed: Jan. 3, 2007

(86) PCT No.: PCT/GB2007/000009
§ 371 (c)(1),
(2), (4) Date: Nov. 6, 2008

(87) PCT Pub. No.: WO2007/077443
PCT Pub. Date: Jul. 12, 2007

(65) Prior Publication Data
US 2009/0187020 A1    Jul. 23, 2009

(30) Foreign Application Priority Data
Jan. 4, 2006 (IN) .............................. 17/MUM/2006

(51) Int. Cl.
*C07D 227/04* (2006.01)
*C07D 211/06* (2006.01)
(52) U.S. Cl. .......................................... 546/16; 546/189
(58) Field of Classification Search .................... 546/16, 546/189
See application file for complete search history.

(56) References Cited

U.S. PATENT DOCUMENTS 4,895,841 A    1/1990    Sugimoto et al.

FOREIGN PATENT DOCUMENTS

| EP | 0296560 | A2 | 12/1988 |
| EP | 1531151 | A1 | 5/2005 |
| EP | 1568688 | A1 | 8/2005 |
| WO | 9722584 | A1 | 6/1997 |
| WO | 0009483 | A2 | 2/2000 |
| WO | 2005003092 | A1 | 1/2005 |
| WO | 2005076749 | A2 | 8/2005 |
| WO | 2007077443 | A1 | 7/2007 |

OTHER PUBLICATIONS

Foreign communication from a related counterpart application—International Search Report and Written Opinion PCT/GB/2007/000009, Mar. 1, 2007, 12 pages.
Foreign communication from the priority application—International Preliminary Report on Patentability, PCT/GB2007/000009, Jul. 8, 2008, 6 pages.

*Primary Examiner* — Rita Desai
(74) *Attorney, Agent, or Firm* — Conley Rose, P.C.; Rodney B. Carroll

(57) ABSTRACT

The invention relates to new compounds of formula (III):

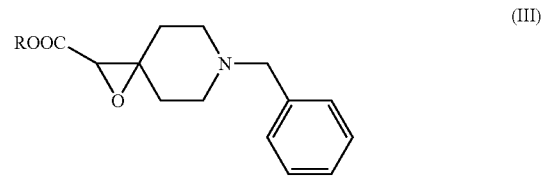

wherein R is a $C_1$-$C_4$ linear or branched alkyl group.

The invention also relates to new compounds of formula (IV)

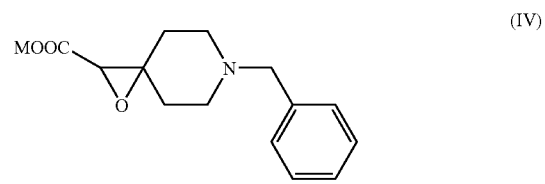

wherein M is a metal.

The invention also relates to methods of making compounds of formulas (III) and (IV) and to methods of making donepezil and pharmaceutically acceptable salts thereof, such as donepezil hydrochloride, using the compounds.

20 Claims, No Drawings

PROCESS AND INTERMEDIATE FOR PREPARATION OF DONEPEZIL

CROSS-REFERENCE TO RELATED APPLICATIONS

This application is a filing under 35 U.S.C. 371 of International Application No. PCT/GB2007/000009 filed Jan. 3, 2007, entitled "Process and Intermediate for Preparation of Donepezil," claiming priority of Indian Patent Application No. 17/MUM/2006 filed Jan. 4, 2006, which applications are incorporated by reference herein in their entirety.

FIELD OF THE INVENTION

The present invention relates to new process for the synthesis of acetylcholinesterase inhibitors. The invention additionally relates to novel synthetic intermediate used in this process and preparation thereof.

BACKGROUND OF THE INVENTION

U.S. Pat. No. 4,895,841 discloses donepezil hydrochloride (I), chemically known as (±)-2,3-dihydro-5,6-dimethoxy-2-[[1-(phenylmethyl)-4-piperidinyl]methyl]-1H-inden-1-one hydrochloride, as cyclic amine compounds.

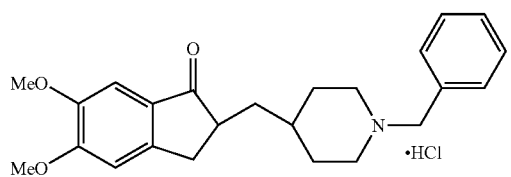

(I)

Donepezil hydrochloride (I) is a reversible inhibitor of the enzyme acetylcholinesterase useful in the treatment of mild to moderate dementia of the Alzheimer's type disease.

N-benzyl 4-formyl piperidine (II) is a key intermediate in the synthesis of donepezil.

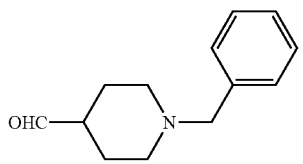

(II)

The intermediate (II) can be obtained by using (methoxymethyl) triphenyl phosphonium chloride as a reagent as disclosed in EP0296560. However, this reaction is not only very expensive, but requires the reaction to take place under cryogenic conditions. Another method, such as disclosed in U.S. Pat. No. 4,895,841, employs pyridine-4-aldehyde in the synthesis of intermediate (II), which is followed by reduction of aromatic ring at last stage also involves very harsh reaction conditions.

There are many other processes known in the art to prepare donepezil hydrochloride, which are exemplified in patent applications such as WO2005076749, EP1531151 and WO2005003092.

The present invention is novel and relates to synthesis of donepezil hydrochloride using a novel synthetic intermediate. Thus, the object of the present invention is to provide a simple and industrially viable process for the synthesis of donepezil hydrochloride using a novel intermediate. This invention enables the synthesis of donepezil to be carried out in a cost effect manner and avoiding unfavorable reaction conditions.

SUMMARY OF THE INVENTION

Broadly, the present invention relates to a process for preparing donepezil and salts thereof using a novel intermediate.

According to one aspect of the invention there is provided a process for preparing a compound of formula (III):

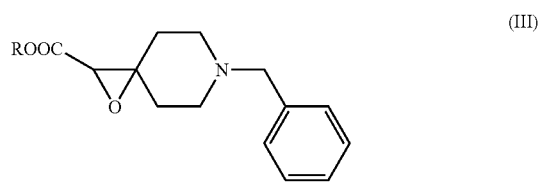

(III)

wherein R is a $C_1$-$C_4$ linear or branched alkyl group, said process comprising reacting N-benzyl 4-piperidone with a compound of formula (V):

X—CH$_2$COOR'  (V)

wherein X is Cl, Br or I, and R' is a $C_1$-$C_6$ linear or branched alkyl group.

According to another aspect of the invention there is provided a process for the preparation of a compound of formula (IV):

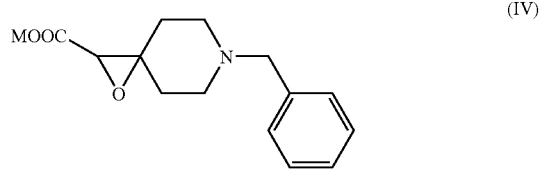

(IV)

wherein M is an alkali metal, said method comprising preparing a compound of formula (III) using a process as described above, then reacting the compound of formula (III) with a base in the presence of a solvent.

According to another aspect of the invention there is provided a process for preparing a compound of formula (II):

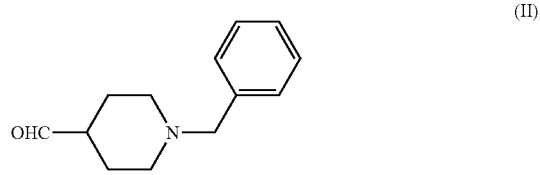

(II)

said process comprising preparing a compound of formula (IV) by a process as described above, then adding an acid to form the compound of formula (II).

According to another aspect of the invention there is provided a process for preparing donepezil or a pharmaceutically acceptable salt thereof, comprising (i) preparing a compound of formula (II) by a process according to any one of claims 12 to 14; (ii) reaction the compound of formula (II) prepared in step (i) with 5,6-dimethoxy indanone to produce 1-Benzyl-4-[(5,6 dimethoxy-1-indanon)-2-ylidenylmethyl piperidine; (iii) hydrogenation of the 1-Benzyl-4-[(5, 6 dimethoxy-1-indanon)-2-ylidenylmethyl piperidine produced in step (ii) in the presence of a catalyst to produce 1-Benzyl-4-[(5,6 dimethoxy-1-indanoyl)-2-yl]methyl-piperidine; and, optionally, (iv) conversion of the 1-Benzyl-4-[(5,6 dimethoxy-1-indanoyl)-2-yl]methyl-piperidine produced in step (iii) to a pharmaceutically acceptable salt thereof. Preferably the salt is the hydrochloride salt.

According to another aspect of the invention there is provided a compound of formula (III):

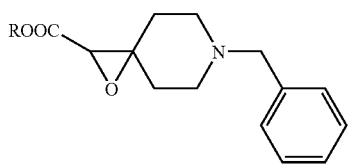

(III)

wherein R is a $C_1$-$C_6$ linear or branched alkyl group.

According to another aspect of the invention there is provided a compound of formula (IV):

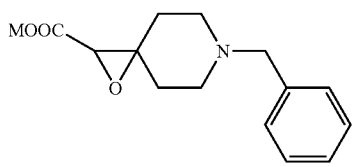

(IV)

wherein M is an alkali metal.

DETAILED DESCRIPTION

In one aspect, the present invention provides a process for the synthesis of donepezil and salts thereof, which is synthesized through a key intermediate N-benzyl 4-formyl piperidine (II) which is itself synthesised prepared via an intermediate of formula (III):

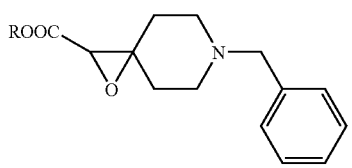

(III)

where R=$C_1$-$C_6$ alkyl chain, linear or branched. Preferably, R=$C_1$-$C_4$ alkyl chain, linear or branched. Most preferably R is ethyl. This process involves use of cheaper and readily available commercial reagents which makes the process industrially economical with high yield and purity of donepezil hydrochloride (I).

In another aspect, the present invention provides a new and efficient process for synthesizing N-benzyl 4-formyl piperidine (II) using the intermediate of formula (III).

In yet another aspect, the present invention provides compounds of the Formula (III) and a process for the preparation thereof. The process involves reaction of N-benzyl 4-piperidone with X—$CH_2COOR^1$ where X=chloro, bromo, iodo and $R^1$ is a linear or branched $C_1$-$C_6$ alkyl chain, preferably a linear or branched $C_1$-$C_4$ alkyl chain, in a suitable solvent and in presence of base. The base is preferably an alkali metal alkoxide, and alkali metal amide or an alkyl lithium. The alkoxide is preferably a $C_1$-$C_6$ alkoxide, more preferably a $C_1$-$C_4$ alkoxide, and most preferably a methoxide or ethoxide. The alkyl group of the alkyl lithium is preferably a $C_1$-$C_6$ alkyl, more preferably a $C_1$-$C_4$ alkyl, and most preferably methyl or ethyl. The following materials are, for example, suitable for use as the base: sodium methoxide, sodium ethoxide, sodium amide, n-butyl Lithium, lithium di-isopropyl amide (LDA), etc. or mixtures thereof. The solvent employed for this reaction is preferably selected from benzene, toluene, xylenes, dioxane or THF or mixtures thereof.

The reaction to form the compound (III) has a specific advantage that it can be carried out at temperatures above 0° C., i.e., it does not have to be carried out at cryogenic temperatures. The reaction temperature is suitably in the range 10° C. to 30° C.

The glycidic ester (III) may be further converted into the alkali metal salt, preferably sodium, of glycidic acid (IV) in a suitable organic solvent, in presence of a base.

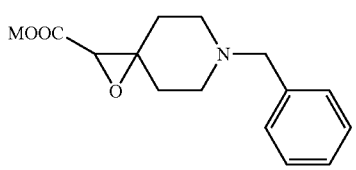

(IV)

where preferably M = Li, Na or K

The base used in the reaction with the compound of formula (III) is an alkali metal alkoxide, or an alkali metal hydroxide. The alkoxide is preferably a $C_1$-$C_6$ alkoxide, more preferably a $C_1$-$C_4$ alkoxide, and most preferably a methoxide or ethoxide. The alkali metal is preferably lithium, sodium or potassium. Sodium methoxide is particularly suitable as the base.

The solvent used in the reaction with the compound of formula (III) is preferably an alcohol, preferably a $C_1$-$C_6$ alcohol, more preferably a $C_1$-$C_4$ alcohol, and most preferably ethanol.

The reaction to form the compound (IV) has a specific advantage that it can be carried out at temperatures above 0° C., i.e., it does not have to be carried out at cryogenic temperatures. The reaction temperature is suitably in the range 10° C. to 30° C.

The metal salt of the glycidic acid (IV) may then be converted into the N-benzyl 4-formyl piperidine (II) in the presence of any aqueous mineral acid at a temperature range of about 25-90° C.; this reaction is known as Darzen's reaction. The N-benzyl 4-formyl piperidine (II) may be further reacted with 5,6-dimethoxy indanone. The resulting product is preferably reduced with palladium on carbon to produce donepezil free base. The donepezil free base may then be optionally converted to a pharmaceutically acceptable salt, such as donepezil hydrochloride (I).

EXAMPLES

The following examples illustrate specific aspects of the present invention. The examples are not intended to limit the scope of the invention in any of the aspects.

Example 1

Preparation of N-1-Benzyl-4 (2'-ethyl carboxylate) epoxy piperidine

To a 500 ml flask fitted with a nitrogen inlet and $CaCl_2$ guard tube, 300 ml of dry toluene was added. To this, was added a mixture of 100 g (0.529 mol) N-benzyl 4-piperidone and 65.0 g (0.53 mol) ethyl chloroacetate. The contents were chilled to −5 C and sodium amide 31.0 g (0.793 mol) was added in lots over a period of 2 h with the temperature maintained between below 0° C. Once the addition was over, the contents were warmed to room temperature (about 25° C.) and stirred for 2 h. The reaction mass was slowly poured into a beaker filled with crushed ice and extracted into 500 ml ethyl acetate. The organic layer was washed with 3 portions of 400 ml water with the last portion containing 6 ml acetic acid. The organic layer was dried over anhydrous sodium sulphate and then concentrated under vacuum to yield 102.0 g of the crude glycidic ester (70% yield), which was used as such for further step without any purification.

Example 2

Preparation of N-1-Benzyl-4(2'-sodium carboxylate) epoxy piperidine-5-carboxylic acid The glycidic ester from Example 1 was slowly poured into a 15° C. solution of sodium methoxide in ethanol and then warmed to room temperature (22° C.) and stirred overnight to obtain a solid. The solid was filtered off under vacuum and washed with 50 ml ethanol, followed by 50 ml diethyl ether. The off-white solid weighed 88.0 g (85%).

Example 3

Preparation of N-benzyl 4-formyl piperidine

The sodium salt from example 2 was dissolved in 250 ml water containing 50 ml HCl and heated reflux temperature (at about 90° C.) and maintained for 2 hours. The reaction mass was then cooled to 15° C. with the aid of ice-water and liquor ammonia slowly added to the solution to render the pH alkaline. The contents were extracted into 300 ml dichloro methane, washed with water and dried over anhydrous sodium sulphate. The organic layer was concentrated under vacuum to yield yellow coloured oil. 45 g (68% yield).

Example 4

Preparation of 1-Benzyl-4-[(5,6 dimethoxy-1-indanon)-2-ylidenylmethyl piperidine To a solution of 1.0 g of 5,6 dimethoxy indanone dissolved in 25 ml THF, 0.562 g of sodium methoxide was added. The reaction contents were heated to 60° C. and maintained for 30 min before cooling to 10° C. A solution of 1.1 g of N-benzyl 4-formyl piperidine dissolved in 25 ml THF was then added drop-wise over a period of 30 min keeping the temperature less than 10° C. After complete addition, the reaction was slowly warmed to 25-30° C. and stirred for 3 h. The reaction mass was quenched in cold water and extracted with 100 ml of ethyl acetate. The organic layer was washed with 2×100 ml water and 100 ml of sodium chloride solution and dried over anhydrous sodium sulphate. The organic layer was concentrated under vacuum to obtain an off-white solid (1.4 g, 71% yield).

Example 5

Preparation of 1-Benzyl-4-[(5,6 dimethoxy-1-indanoyl)-2-yl]methyl-piperidine hydrochloride (donepezil hydrochloride)

1.0 g of 1-Benzyl-4-[(5,6 dimethoxy-1-indanon)-2-ylidenylmethyl piperidine was dissolved in 50 ml of ethanol and 100 mg of 10% palladium on carbon added to it. The reaction mass was subjected to 10 psi hydrogen pressure for 1 h. The catalyst was then filtered off and the filtrate was concentrated to residue, which was dissolved in 100 ml of ethyl acetate and cooled to 15° C. further 10 ml conc.HCl was added and the resulting solid filtered, washed with diethyl ether and dried under vacuum. The solid weighed 0.9 g (81% yield).

Example 6

Preparation of 1-Benzyl-4-[(5,6 dimethoxy-1-indanoyl)-2-yl]methyl-piperidine hydrochloride (donepezil hydrochloride)

Step-a—1-Benzyl 4-epoxy-4-α-carboxyethyl piperidine

A solution of 1 kg of N-benzyl 4-piperidone and 648 g of ethyl chloro acetate in 3 L of toluene were cooled to 10° C. and 310 g of sodamide was added portionwise over a period of 1.5 h. After completion of addition the reaction mass was warmed to 25-30° C. and stirred for 3 hrs. The reaction mass was poured into a beaker containing crushed ice and extracted into 5 L of ethyl acetate. The ethyl acetate layer was washed with 3×2.5 L of water containing 60 ml of acetic acid. The organic layer is then washed with 2.5 L of brine solution and dried over anhydrous sodium sulphate. The organic layer was concentrated under vacuum to yield a yellow colored oil weighed 1 kg.

Step-b—Sodium salt of 1-Benzyl 4-epoxy-4-α-carboxyethyl piperidine 1 kg of step-a product was dissolved in 500 ml of 95% ethanol and slowly added to a cold solution of 235 g of sodium methoxide in 500 ml of 95% ethanol. After the addition, the solution was warmed to 25-30° C. and stirred overnight to obtain a white solid which was filtered and suck-dried. Yield 785 g.

Step-c—N-benzyl 4-formyl piperidine 785 g of step-b product was dissolved in 2.3 L of water and 418 ml of conc.HCl added to it slowly. The mixture was refluxed for 1.5 h and then cooled to 15° C. and liq.NH$_3$ added to it till pH=8.5-9.0. The contents were extracted into 2.5 L of chloroform and washed with water and brine. The organic layer was dried over sodium sulphate and concentrated to obtain light yellow oil (88.5 gm)

Step-d—1-Benzyl-4-[(5,6 dimethoxy-1-indanon)-2-ylidenylmethyl piperidine 78.5 g of 5,6 dimethoxy indanone was dissolved in 500 ml of THF and 66 g of sodium methoxide added to it. The mixture was heated to 60° C. and kept for 30-45 min before cooling to 5° C. 88.5 g of step-d product was dissolved in 500 ml of THF and added drop-wise over a period of 30 min with temperature maintained 5-10° C. Once the addition was over, the reaction mixture was warmed to room temperature and stirred for 3 h. The reaction mass was poured into cold water and extracted into 2.5 L of ethyl acetate, washed with water and then with brine The organic layer was dried with sodium sulphate and concentrated to obtain a solid (109 g)

Step-e—1-Benzyl-4-[(5,6 dimethoxy-1-indanoyl)-2-yl]methyl-piperidine hydrochloride 109 g of Step-d product was dissolved in 95% ethanol and 11 g of 10% palladium on carbon added to it. The mixture was hydrogenated at 10 psi for 1 h. The catalyst was then filtered off and the filtrate concentrated to residue, the residue was dissolved in 500 ml of ethyl acetate and cooled to 10° C. HCl gas dissolved in IPA was then added to precipitate a solid. The resulting solid was filtered and dried to get 100 g of 1-Benzyl-4-[(5,6 dimethoxy-1-indanoyl)-2-yl]methyl-piperidine hydrochloride Having described the objects of the invention with reference to the examples it is to be understood that the examples and descriptions herein are proffered by way of example to facilitate comprehension of the invention and should not be construed to limit the scope thereof. Any person skilled in the art could effect various changes and modifications without departing from the scope of the present invention.

The invention claimed is:

1. A process for preparing a compound of formula (III):

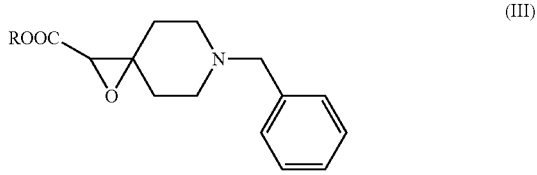

(III)

wherein R is a $C_1$-$C_6$ linear or branched alkyl group, said process comprising reacting N-benzyl 4-piperidone with a compound of formula (V):

X—$CH_2$COOR'    (V)

wherein X is Cl, Br or I, and R' is a $C_1$-$C_6$ linear or branched alkyl group.

2. The process according to claim 1, wherein said reaction is carried out in the presence of a base.

3. The process according to claim 2, wherein said base is an alkali metal alkoxide, and alkali metal amide or an alkyl lithium.

4. The process according to claim 1, wherein said reaction is carried out in the presence of a solvent.

5. The process according to claim 4, wherein said solvent is benzene, toluene, xylene, dioxane, THF or a mixture thereof.

6. The process of claim 1 further comprising preparing a compound of formula (IV):

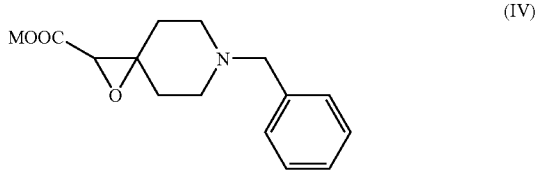

(IV)

wherein M is an alkali metal, said method comprising preparing a compound of formula (III) using a process according to claim 1, then reacting the compound of formula (III) with a base in the presence of a solvent.

7. The process according to claim 6, wherein said base used in the reaction with the compound of formula (III) is an alkali metal alkoxide, or an alkali metal hydroxide.

8. The process according to claim 7, wherein said base used in the reaction with the compound of formula (III) is an alkali metal methoxide.

9. The process according to claim 6, wherein said alkali metal is lithium, sodium or potassium.

10. The process according to claim 6, wherein said solvent used in the reaction with the compound of formula (III) is a $C_1$-$C_6$ alcohol.

11. The process according to claim 10, wherein said solvent used in the reaction with the compound of formula (III) is an ethanol.

12. The process of claim 1 further comprising preparing a compound of formula (II):

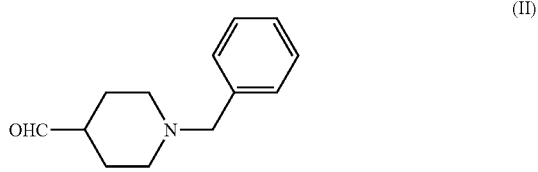

(II)

said process comprising preparing a compound of formula (IV) by a process according to claim 1, then adding a mineral acid to form the compound of formula (II).

13. The process according to claim 12, wherein the mineral acid is hydrochloric acid, sulphuric acid or phosphoric acid.

14. The process according to claim 12, wherein the reaction with the compound of formula (IV) is carried out at a temperature in the range 25° C. to 90° C.

15. The process of claim 12 further comprising preparing donepezil or a pharmaceutically acceptable salt thereof, comprising (i) preparing a compound of formula (II) by a process according to claim 12; (ii) reaction the compound of formula (II) prepared in step (i) with 5,6-dimethoxy indanone to produce 1-Benzyl-4-[(5,6 dimethoxy-1-indanon)-2-ylidenylmethyl piperidine; (iii) hydrogenation of the 1-Benzyl-4-[(5,6 dimethoxy-1-indanon)-2-ylidenylmethyl piperidine produced in step (ii) in the presence of a catalyst to produce 1-Benzyl-4-[(5,6 dimethoxy-1-indanoyl)-2-yl]methyl-piperidine; and, optionally, (iv) conversion of the 1-Benzyl-4-[(5,6 dimethoxy-1-indanoyl)-2-yl]methyl-piperidine produced in step (iii) to a pharmaceutically acceptable salt thereof.

16. The process according to claim 15, wherein said salt is the hydrochloride salt.

17. The process of claim 12 further comprising preparing donepezil hydrochloride comprising (i) preparing a compound of formula (II) by a process according to claim 12; (ii) reaction the compound of formula (II) prepared in step (i) with 5,6-dimethoxy indanone to produce 1-Benzyl-4-[(5,6 dimethoxy-1-indanon)-2-ylidenylmethyl piperidine; (iii) hydrogenation of the 1-Benzyl-4-[(5,6 dimethoxy-1-indanon)-2-ylidenylmethyl piperidine produced in step (ii) in the presence of a catalyst to produce 1-Benzyl-4-[(5,6 dimethoxy-1-indanoyl)-2-yl]methyl-piperidine; and (iv) conversion of the 1-Benzyl-4-[(5,6 dimethoxy-1-indanoyl)-2-yl]methyl-piperidine produced in step (iii) to 1-Benzyl-4-[(5,6 dimethoxy-1-indanoyl)-2-yl]methyl-piperidine hydrochloride.

18. The process according to claim 16, wherein in step (iv) the conversion of the 1-Benzyl-4-[(5,6 dimethoxy-1-indanoyl)-2-yl]methyl-piperidine produced in step (iii) to 1-Benzyl-4-[(5,6 dimethoxy-1-indanoyl)-2-yl]methyl-piperidine hydrochloride is carried out by the addition of HCl.

19. A compound of formula (IV):

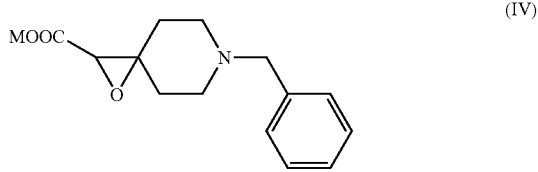

(IV)

wherein M is an alkali metal.

20. The compound according to claim 19, wherein the alkali metal is lithium, sodium or potassium.

* * * * *